(12) United States Patent
Pirrie

(10) Patent No.: US 7,337,993 B2
(45) Date of Patent: Mar. 4, 2008

(54) ELECTROSTATIC ATOMISATION DEVICE

(75) Inventor: Alastair Bruce Pirrie, Oxford (GB)

(73) Assignee: Aerstream Technology, Ltd., Oxon (GB)

( * ) Notice: Subject to any disclaimer, the term of this patent is extended or adjusted under 35 U.S.C. 154(b) by 508 days.

(21) Appl. No.: 10/481,583

(22) PCT Filed: Jun. 20, 2002

(86) PCT No.: PCT/GB02/02900

§ 371 (c)(1),
(2), (4) Date: Jun. 29, 2004

(87) PCT Pub. No.: WO03/000431

PCT Pub. Date: Jan. 3, 2003

(65) Prior Publication Data

US 2004/0251326 A1    Dec. 16, 2004

(30) Foreign Application Priority Data

Jun. 22, 2001    (GB) ................................ 0115355.0

(51) Int. Cl.
*B05B 5/00*    (2006.01)
*F23D 11/32*    (2006.01)
*A61M 13/00*    (2006.01)

(52) U.S. Cl. ........................ 239/690; 239/703; 239/706; 239/692; 239/3; 604/58; 128/200.14; 128/200.12

(58) Field of Classification Search ................. 239/690, 239/690.1, 692, 695, 696, 703, 706, 708; 128/203.12, 203.15, 203.17; 604/58
See application file for complete search history.

(56) References Cited

U.S. PATENT DOCUMENTS

| | | |
|---|---|---|
| 4,581,675 A | 4/1986 | Kelly |
| 5,503,335 A | 4/1996 | Noakes et al. |
| 5,511,726 A * | 4/1996 | Greenspan et al. ...... 239/102.2 |

(Continued)

FOREIGN PATENT DOCUMENTS

EP    853 980 A2    7/1998

(Continued)

*Primary Examiner*—Kevin Shaver
*Assistant Examiner*—James S. Hogan
(74) *Attorney, Agent, or Firm*—Ted Sabety

(57) ABSTRACT

An atomization device comprises a conduit containing liquid to be atomized, a spray electrode (1) and a discharge electrode (3). Each electrode is adjacent to a dielectric (5) and they are connected in an electrical circuit (10) to enable a potential difference to be applied between them to atomize the liquid and to generate charge carriers of a first polarity in the proximity of the spray electrode (1) and ions of a second polarity in the proximity of the discharge electrode (3). Some of the first polarity charge carriers deposit on the dielectric adjacent to the spray electrode (1) and some of the second polarity ions deposit on the dielectric (5) adjacent to the discharge electrode (3) so that the atomized liquid is repelled from the dielectric (5) adjacent to the spray electrode (1) and electrically discharged by second polarity ions that are repelled by the dielectric (5) adjacent to the discharge electrode (3).

62 Claims, 4 Drawing Sheets

U.S. PATENT DOCUMENTS

Figure 1:
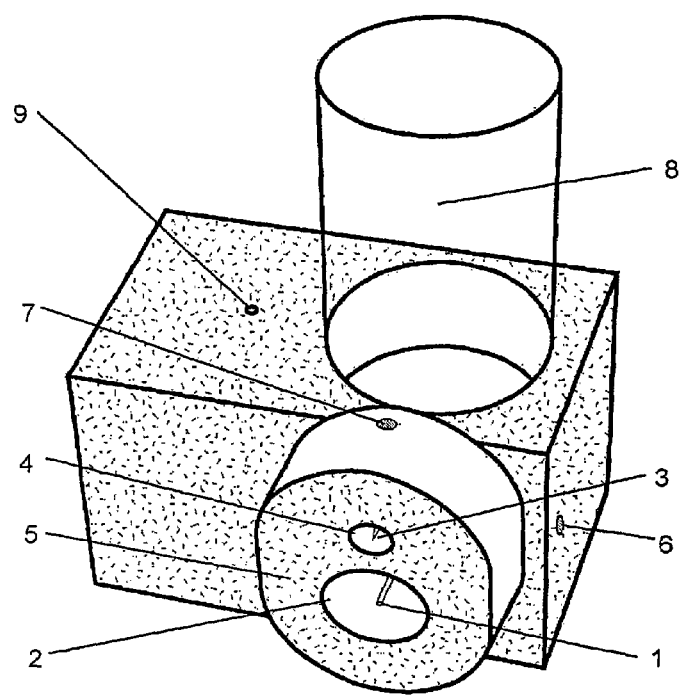

| | | | |
|---|---|---|---|
| 5,810,265 A | | 9/1998 | Cornelius et al. |
| 5,840,074 A | * | 11/1998 | Ayer et al. ............... 604/892.1 |
| 5,927,618 A | | 7/1999 | Jefferies et al. |
| 6,076,519 A | * | 6/2000 | Johnson ................ 128/200.14 |
| 6,135,369 A | * | 10/2000 | Prendergast et al. ........ 239/690 |
| 6,394,086 B1 | * | 5/2002 | Barnes et al. .......... 128/203.15 |
| 6,454,193 B1 | * | 9/2002 | Busick et al. ............... 239/690 |
| 6,657,470 B1 | * | 12/2003 | Latham et al. .............. 327/202 |
| 6,684,879 B1 | * | 2/2004 | Coffee et al. .......... 128/200.14 |

FOREIGN PATENT DOCUMENTS

| | | |
|---|---|---|
| WO | WO 96/10331 A1 | 4/1996 |
| WO | WO 00/35524 A2 | 6/2000 |

* cited by examiner

ELECTROSTATIC ATOMISATION DEVICE

The invention relates to a simple, robust device for the atomisation of chemicals through the generation of a high specific surface area of a liquid by electronic means.

A similar process occurs in nature under the influence of the electrical potential created by the Earth's natural voltage field and enhanced during atmospheric disturbances, whereby a concentration of the electric field drives liquid into the surrounding air, such as with charged water droplets or fragrance glands on plants.

WO92/15339 describes how artificial high-voltages can be used to atomise or vaporize liquids, much in the same way that it occurs in nature. This technique is known as an electrospray or electrohydrodynamic (EHD) spraying. However, a device such as this has a significant disadvantage since it forms charged particles of liquid which are driven by the electric field towards the earthed surroundings near the device and collect in its local vicinity even when a powerful fan is used to try to drive the droplets further away. The device is also bulky which limits its uses in some applications, such as for a portable device.

A later patent, U.S. Pat. No. 5,337,963, describes a similar device, based on the same principle, which teaches only that a capillary can be used to draw liquid up from a reservoir. This device, although undoubtedly smaller than the previous example, nevertheless suffers from the same problem of electrically driven deposition to any earthed surfaces around the device.

Such deposition can be a serious problem for an atomisation device such as one used to disperse an aroma, for example. Aromatic oils are often corrosive to plastics, varnishes and other quality finishes and may cause softening, crazing and/or discolouring of the surface material. For industrial devices this is not always a significant problem where, for instance, the device is placed inside a metal duct. However, in a domestic environment it can cause long-term damage to surfaces over the lifetime of the device. Furthermore, liquid deposited around the device does not evaporate as efficiently as when it is airborne, and so the efficiency of these devices is less than ideal. It is also difficult to control the dispersion of a fragrance, since the deposited material continues to disperse fragrance long after the device is switched off.

Such electrically driven deposition seriously reduces the efficiency of the device and might pose a health risk if this deposition led to uncontrolled contact with active chemicals or pharmaceuticals delivered by the device.

The simplest solution is to use ions of the opposite polarity to discharge the liquid spray as described in GB-A-2018627. However, this method has been found to have many shortcomings. In particular, the spray rapidly contaminates the discharging electrode reducing its effectiveness and causing liquid build-up and dripping. Consequently, this method cannot be used for many practical applications.

One solution to this is to use a third electrode, for instance as described in WO0064590 and GB2327895. However, the placement of electrodes is sensitive to changes of the order of 0.5 mm and the electrode voltages must be specified with an accuracy of the order of 5%.

According to one aspect of the invention there is provided an atomisation device comprising:

a) a conduit that contains, in use, liquid to be atomised;
b) a spray electrode; and,
c) a discharge electrode;

each electrode being adjacent to a dielectric, wherein the electrodes are connected in an electrical circuit to enable a potential difference to be applied between the spray electrode and the discharge electrode to atomise the liquid and to generate charge carriers of a first polarity in the proximity of the spray electrode and ions of a second polarity in the proximity of the discharge electrode, and wherein some of the first polarity charge carriers deposit on the dielectric adjacent to the spray electrode and some of the second polarity ions deposit on the dielectric adjacent to the discharge electrode so that the atomised liquid is repelled from the dielectric adjacent to the spray electrode and electrically discharged by second polarity ions that are repelled by the dielectric adjacent to the discharge electrode.

Hence, by careful placement of material and electrodes a robust device can be built which overcomes all these problems and also has many other useful attributes.

Furthermore, with the geometry described, electrode voltages can vary by 30% or more, and the electrodes can be moved by distances of 1 to 2 mm. This means that production tolerances are lower, the device is more robust to changes in environmental conditions (such as temperature and humidity) as well as formulation properties (such as electrical conductivity, permittivity, surface tension and viscosity) all of which are generally described in the art as fundamental parameters for devices of this kind.

In a preferred embodiment, the atomisation device further comprises a housing made of dielectric material defining respective recesses in which the electrodes are mounted. Normally, the electrodes are substantially flush with the top of the recesses.

Typically, the conduit is the spray electrode and it may be made from a conductive plastic.

The atomisation device functions irrespective of the relative polarity of the two electrodes. However, the first polarity is typically positive whilst the second polarity is typically negative.

The atomisation device requires a supply of liquid to be atomised and this may be provided by a reservoir connected to the conduit, the reservoir for containing the liquid to be atomised. In this case, the liquid to be atomised may be conveyed from the reservoir to the conduit in a variety of ways. For instance, the liquid to be atomised may be conveyed from the reservoir to the conduit using a pump, by capillary action or under the influence of gravity.

In one embodiment, the atomisation device may comprise a plurality of reservoirs, each reservoir being connected to a respective pump that conveys liquid to be atomised from each reservoir to the conduit.

A further embodiment of this invention is an atomisation device comprising a plurality of conduits and spray electrodes and in this case, the atomisation device may further comprise a plurality of reservoirs, each reservoir being connected to a corresponding conduit.

The dielectric material is selected such that it leaks charge at a slow rate, ensuring that the dielectric retains a slight charge of the same polarity as the adjacent electrode. Typically, dielectric material has a surface resistance in the range of $10^4$ to $10^{14}\Omega$ and a bulk resistivity of $10^5$ to $10^{15}$ $\Omega$m.

The dielectric can be manufactured from a variety of materials but, typically, the dielectric material is nylon 6, nylon 11, nylon 12, nylon 66 or a polyacetyl-polytetrafluoroethylene blend.

The dielectric material may be rendered suitable for use in an atomisation device according to this invention by treating the dielectric material such that its surface resistance is in the range of $10^4$ to $10^{14}$ ohms.

In certain circumstances it is desirable to control the flow rate of the fluid flowing through the conduit and as such, the atomisation device may further comprise a measuring system for measuring the flow rate of the liquid flowing through the conduit and a duty cycle modulator connected to the measuring system for controlling the flow rate by adjusting the duty cycle of the potential difference applied between the spray and discharge electrodes.

In this case, the measuring system may comprise a current monitor arranged to measure the current flowing to the spray electrode.

A cap may be fitted to the atomisation device in order to direct the atomised liquid to a predefined region. As such, the atomised liquid can be directed for the purposes of remote odorising or fumigation of a room, for mechanical or human analysis or for personal or individual inhalation.

The cap may have vortex fins to stir the atomised liquid. This has particular utility when the cap is fitted to an atomisation device having a plurality of spray conduits since it assists the mixing of the atomised liquids.

The atomisation device may be used in a wide variety of applications and, in particular, it can be used to atomise aromatic oils, agricultural chemicals, pharmaceutical products and pest control or pesticide products.

Other uses of the atomisation device are to deliver the atomised liquid to a real or artificial nose for analysis or personal inhalation and for remote odorising or fumigation of a room.

A liquid atomised by the device will vaporise according to its vapour pressure amongst other factors and so a further use of the device is to vaporise a liquid by atomising it.

There now follows a description of the invention by way of example, with reference to the accompanying drawings, in which:

FIG. 1 shows an example of a vaporization device embodying this invention;

FIG. 2 shows an example driving circuit, suitable for operating the vaporization device of FIG. 1;

FIG. 3 illustrates schematically one possible configuration of the present invention;

FIG. 4 illustrates schematically a second possible configuration of the present invention;

FIG. 5 illustrates schematically a third possible configuration of the present invention;

FIG. 6 illustrates schematically a fourth possible configuration of the present invention;

FIG. 7 illustrates schematically a vaporisation device having a plurality of spray electrodes as a further configuration of the present invention; and, FIG. 8 shows a mixing nozzle for use with the multi-spray-electrode configuration of FIG. 7.

FIG. 1 illustrates one possible embodiment of the present invention, where a spray electrode 1 is housed inside a spray recess 2 and a discharging electrode 3 is housed inside a discharging recess 4. The spray electrode 1 in this example comprises a 27-gauge, metal or conductive plastic capillary and the discharging electrode 3 comprises a sharp, stainless steel pin, 0.6 mm in diameter.

The two, longitudinal axes of the cylindrical recesses 2 and 4 are perpendicular to a spray outlet surface 5, which is manufactured from a dielectric material. In this example, the material is nylon and the spray outlet surface 5 is flat. However, other materials and curved surfaces can be used provided that there is sufficient charge retention at the spray outlet surface 5 to deflect the spray and charge carriers away from the device and electrodes.

Electrical connections are made via tapped holes 6 and 7, using conducting screws (not shown) which connect to a driving circuit, such as that shown in FIG. 2.

The liquid to be atomised is held in a threaded, glass vial 8 and air is fed into the glass vial 8 to replace the atomised liquid via the small air inlet hole 9.

When this device is energised by a driving circuit, liquid from the glass vial 8 is emitted from the spray electrode 1 in a very fine form, such that it quickly evaporates according to its vapour pressure and the ambient conditions in the vicinity of the device.

FIG. 2 illustrates diagrammatically one possible driving circuit 10 for driving the atomisation device shown in FIG. 1. A low-voltage power source 20, such as a battery ,is connected via a control switch 21 to the input of a high-voltage converter 22. The output terminals of the converter 22 are connected to the electrical conduits 6 and 7 of the device in FIG. 1 as indicated.

A suitable converter for the device is the Q101-5 manufactured by EMCO High Voltage Corporation, 11126 Ridge Road, Sutter Creek Calif. 95685, USA. The input voltage set by the power source 20 can range from 2.5 to 4V. Any converter capable of delivering voltages from 1 to 30KV at roughly 10 μA or less is suitable for operating this device. Higher power converters can also be used although they provide no added benefit and generally require more safety management. Low power devices, such as piezoelectric crystals are ideal, and have distinct benefits such as reduced size and improved safety.

It should be noted that there is no earth reference shown in FIG. 2. This is deliberate since an earth reference can be omitted altogether or applied to any point in the circuit. The polarity of the high voltage output is also immaterial, and for instance a Q101-5 converter can be replaced by a Q101N-5, its negative counterpart, and the device still functions.

Where there is a chance that the electrodes might come into human contact it is necessary to provide safety measures to protect from electrical shock. This is achieved by means of optional resistors 23 and 24, which can be connected between the high voltage converter 22 and the electrode connections 6 and 7 respectively. A suitable value for resistor 23 is 1GΩ and for resistor 24 is 100MΩ, although any values that prevent an electrical shock and allow the device to function normally can be used.

Since the circuit shown in FIG. 2 can be powered by a low voltage power source, the circuit is compatible with any low voltage electronic device or control circuit. Thus, control switch 21 can be such an electronic device or control circuit which can be used to activate the device remotely or adjust its duty cycle or general application.

One example is the periodic delivery of healthcare products such as a decongestant, or olfactory stimulants, repressants, attractants or dispersants to humans or other animals. In this case, control switch 21 can be a timer circuit that activates the device periodically to deliver the healthcare product.

Another example is where the duty cycle is controlled to compensate for changes in the flow rate of liquid. In this example, control switch 21 can be an electronically controlled switch, such as a field effect transistor (FET). The FET can be switched using a microprocessor, pulse width modulator or other means to adjust the duty cycle of the device.

Two methods for adjusting the duty cycle are described here, although other alternative approaches, such as monitoring the pressure head and adjusting the duty cycle accordingly, will be apparent to the person skilled in the art.

The first method is simply to measure how the flow rate Q varies as a function of running time t from when the device is first activated and the glass vial 8 is full until the glass vial 8 is empty. This provides a function Q(t). The duty cycle as a function of time Ψ(t) can then be set to be Ψ(t)=(Ψ[t=0]×Q[t=0])/Q(t), where Q[t=0] and Ψ[t=0] represent the values of Q(t) and Ψ(t) at the time the device is first activated, such that the chemical output is roughly constant.

An alternative and more accurate method involves monitoring the electrical current i at the spray electrode and adjusting the duty cycle so that $i^2\Psi$ remains constant. The current can be monitored by measuring the voltage across a resistor 25 placed in series with resistor 23, for example.

Figure 2:
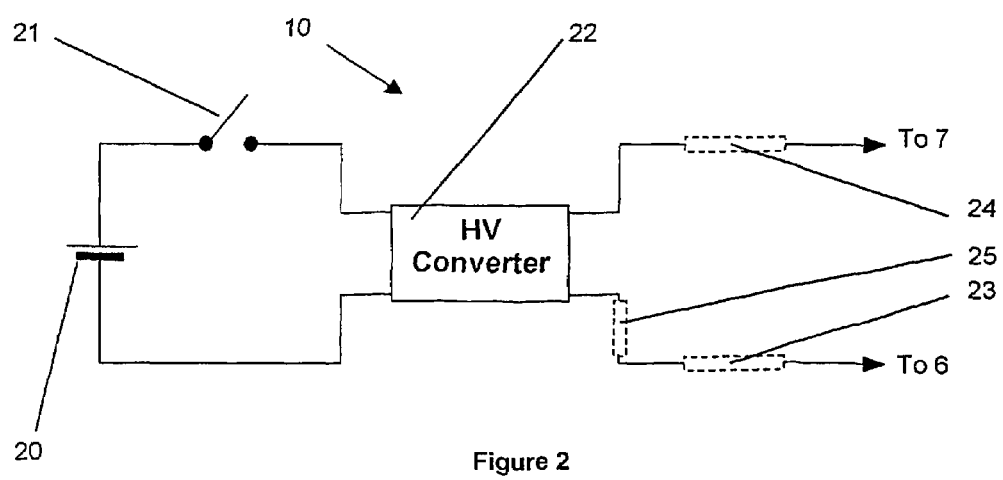

A further modification of the circuit shown in FIG. 2 allows the power source 20 to be replaced by a capacitor or rechargeable battery and an alternative power generation unit such as a solar cell. Renewable power sources, such as this, provide unlimited power under many practical operating conditions, such as the domestic environment, providing reduced servicing costs to the user who need not pay for replacement batteries.

FIG. 3 shows a diagrammatic, part-cross-sectional view, of the outlet surface 34 of the atomisation device shown in FIG. 1 with a schematic illustration of an alternative liquid reservoir which instead comprises a flexible bag 30.

This flexible bag 30 can be made from any flexible, liquid-tight material, and where the liquid contains solvents or other aggressive materials it can be given a metal coating such as manufactured by Ultimet Films Limited, 16 Maurice Gaymer Road, Attleborough, Norfolk, NR17 2QZ, UK.

In this example, the liquid is driven to spray electrode 32 by means of a pump 31, such as described in U.S. Pat. No. 5,876,187. The advantage of such a system is that delivery to spray electrode 1 is set by the pump 31 irrespective of the properties of the liquid and the quantity of liquid remaining in the flexible bag 30. The pump 31 may also deliver multiple shots of predetermined volumes of liquid, for periodic or occasional, controlled doses of chemicals or chemical blends, such as for pest control or other human or animal applications.

The spray electrode 1 and discharging electrode 3 are housed inside cylindrical recesses 2 and 4 respectively. The diameters of recesses 2 and 4 are 10 mm and 6 mm respectively. The outlet surface 5 is flat and in this instance both electrodes 1 and 3 lie back inside the device by a distance of 0.5 mm from the outlet surface 5. The distance between the two electrodes 1 and 3 is 10 mm, and both electrodes 1 and 3 lie along the longitudinal axes of their respective recesses 2 and 4. Power is provided by means of the driving circuit 10, which is as described with reference to FIG. 2.

When the driving circuit 10 is activated a potential difference is set up between the two electrodes 1 and 3.

If, for example, the spray electrode 1 has a positive polarity with respect to the discharging electrode 3 then the discharging electrode 3 sprays ions of negative polarity onto the dielectric recess 4 and to a certain extent onto the outlet surface 5 in close proximity to recess 4. The surface charge that this creates cannot immediately disperse or conduct away and so an electric field is created which tends to deflect other negative ions away from the spray surface 5 and out into the surrounding air.

At the same time, the electrospray is established and (in this example) positively charged droplets create a space charge just beyond the spray electrode 1. The negative ions deflected from the spray surface 5, which are more numerous and mobile than the droplets, move in the electric field to discharge the charged droplets. These then waft (uncharged) away from the spray surface 5 and evaporate according to their vapour pressure or the vapour pressures of their various constituents. The spray electrode 1 may also create some positively charged ions and, having less inertia, these may land on the recess 2 or the spray surface 5 in close proximity to recess 2. These too will set up an electric field which discourages further deposition of positive charge carriers, comprising ions and charged liquid droplets. In this way, a highly efficient atomisation device is created both in terms of mass transfer and energy consumption.

FIG. 4 shows another diagrammatic, part-cross-sectional view, of an alternative spray surface embodying this invention. Here the reservoir of liquid is open to the atmosphere via small air-inlet hole 41 to minimise diffusion of vapour out of the reservoir. The liquid flows from the reservoir to the spray electrode 42 under the influence of gravity. In this case, the dimensions of the spray electrode 42, shown here as a stainless-steel capillary, must have a small outer diameter so that the surface tension of the liquid retains the liquid in place when the device is not active.

The discharging electrode 43 is a sharp, stainless steel pin 0.6 mm in diameter and resides along the longitudinal axis of a cylindrical recess 46 of only 2 mm diameter, and stands slightly proud (approximately 0.5 mm) of the outlet surface 44, which is made from Delrin, an acetyl-PTFE blend.

The spray electrode 42 resides along the longitudinal axis of a cylindrical recess 45 of 6 mm diameter and is flush with the outlet surface. The outlet surface 44 is horizontal in this example, and sprays downwards, which might be suitable for a closet freshener or moth repellant.

This embodiment is powered by driving circuit 10, connected between the two electrodes 42 and 43, which is as described with reference to FIG. 2. This embodiment has the advantage of being slightly smaller than the device illustrated in FIG. 3, with the distance between the electrodes being only 6 mm, thus illustrating that the device can be made extremely small.

FIG. 5 shows another diagrammatic, part-cross-sectional view, of an alternative spray surface embodying this invention. Here the spray surface 54 also lies in a horizontal orientation but sprays upwards and is suitable where the device must sit on a surface, for example, for table-top or bedside devices. The liquid is retained in an upturned, rigid vial 50, such as a glass sampling vial. A small amount of liquid fills a channel 51 (which also acts as an air-feed point to replace liquid) just below the bottom of the glass vial 50 and then enters the spray electrode 52. In this example the internal conduit of the spray electrode 52 must have capillary dimensions, in that liquid must be drawn from the channel 51 to the outlet by surface tension forces alone. For example, if the electrode 52 is a cylindrical tube a suitable inner diameter is 150 μm if the outlet of the spray electrode was 20 mm above the channel 51. However, any suitable conduit dimension d can be selected provided that it meets the following criterion:

$$d < \frac{4\gamma}{\rho g h}$$

where γ is the surface tension of the liquid, p is its density, g is the acceleration due to gravity and h is the vertical height from the channel 51 to the highest point of the spray electrode 52 which in this case is its outlet 58.

In this example, the discharging electrode 53 is conductive plastic 1 mm in diameter and sharpened to a point. It lies along the longitudinal axis of a recess 56, 4 mm in diameter, and is flush with the outlet surface 54. The spray electrode 52 lies along the longitudinal axis of another recess 55, roughly 8 mm in diameter, and stands 0.5 mm proud of the outlet surface 54. Despite the direct path between the tips of the two electrodes, the device functions well due to the larger area of dielectric surrounding the discharging electrode 53 created by spacing the two electrodes 52, 53 further apart. In this example the inter-electrode spacing is 16 mm.

In this example the two recesses 55,56 are not closed but air is free to pass directly through them. This helps prevent eddy currents of air in the vicinity of the outlet surface 54, and helps increase the penetration distance of the diffuse liquid product. Similar effects can be achieved by any air channel in the spray surface 54 and this need not necessarily be provided in the electrode recesses 55,56.

The driving circuit 10, connected between the two electrodes 52 and 53, is as described above with reference to FIG. 2.

Figure 6:
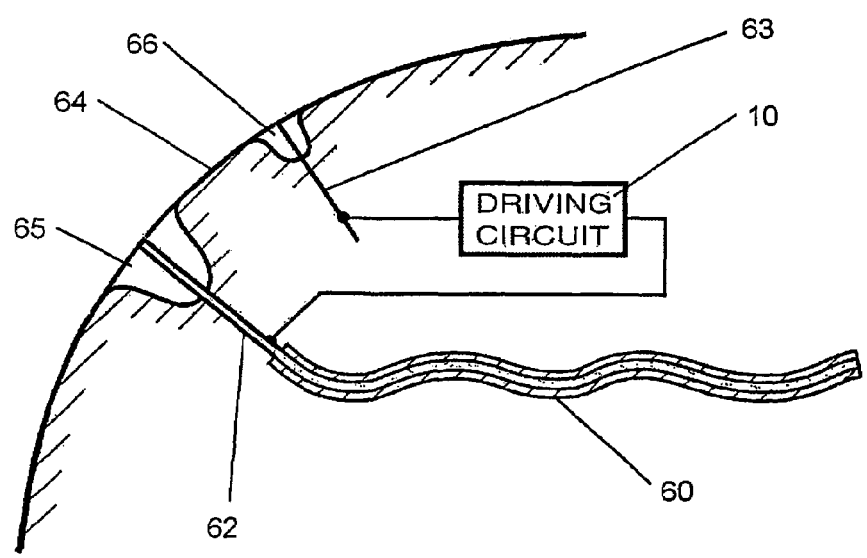

FIG. 6 shows another diagrammatic, part-cross-sectional view, of an alternative spray surface 64 embodying this invention. Here the liquid reservoir is a simple tube 60 for holding small quantities of liquid, although the tube 60 can extend indefinitely and twist or spiral so it takes up less space. The tube 60 connects directly to the spray electrode 62, and this can be merely a continuation of tube 60, if desired.

Figure 3:
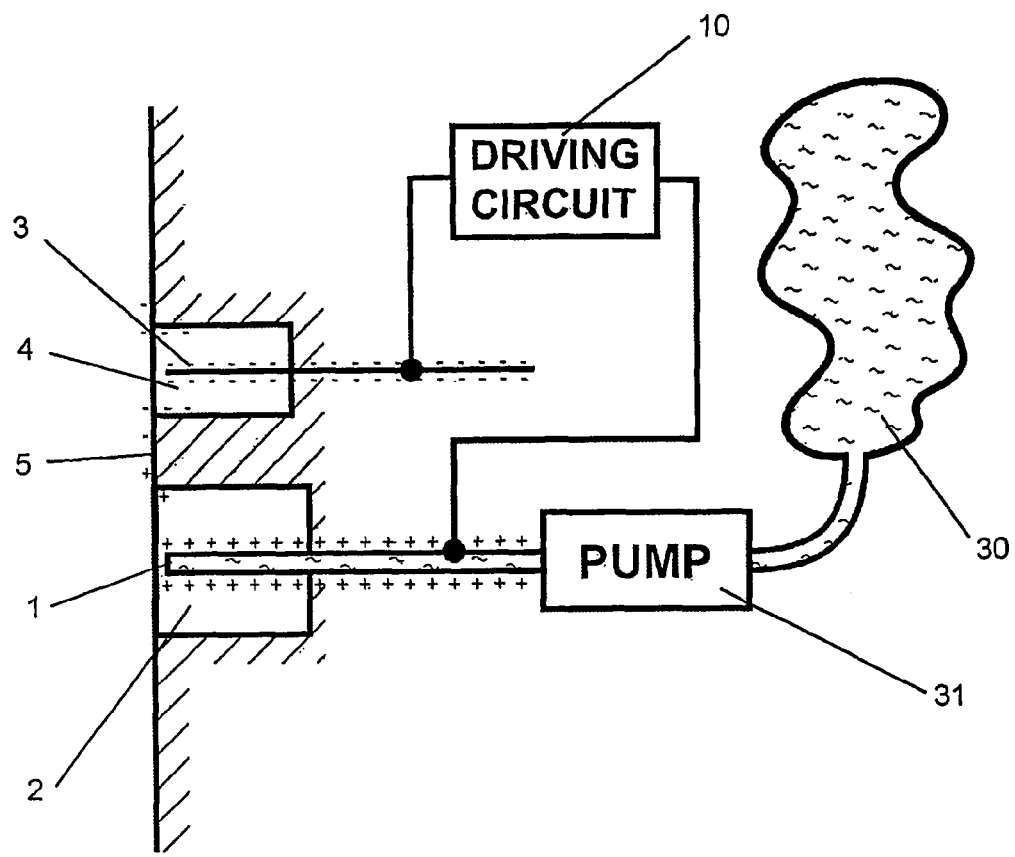
Figure 4:
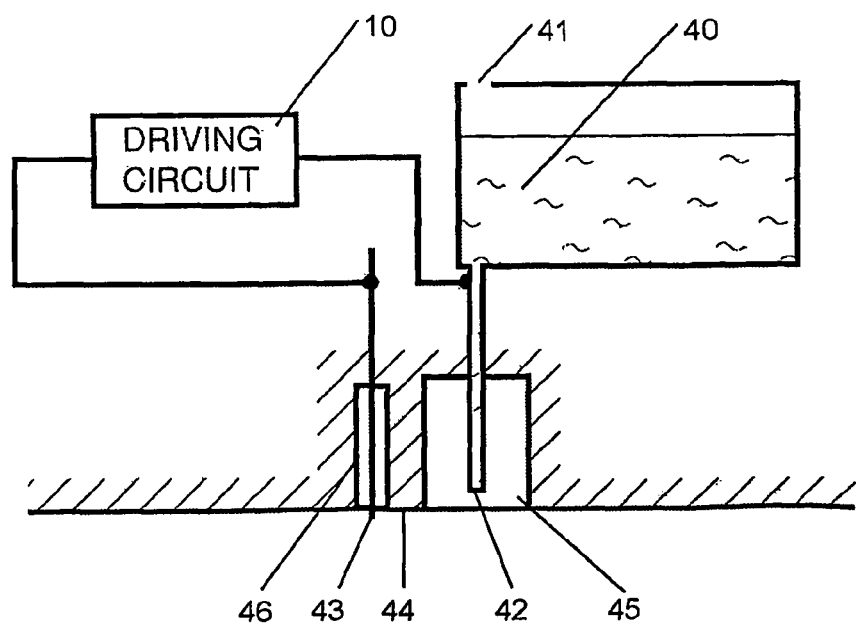
Figure 5:
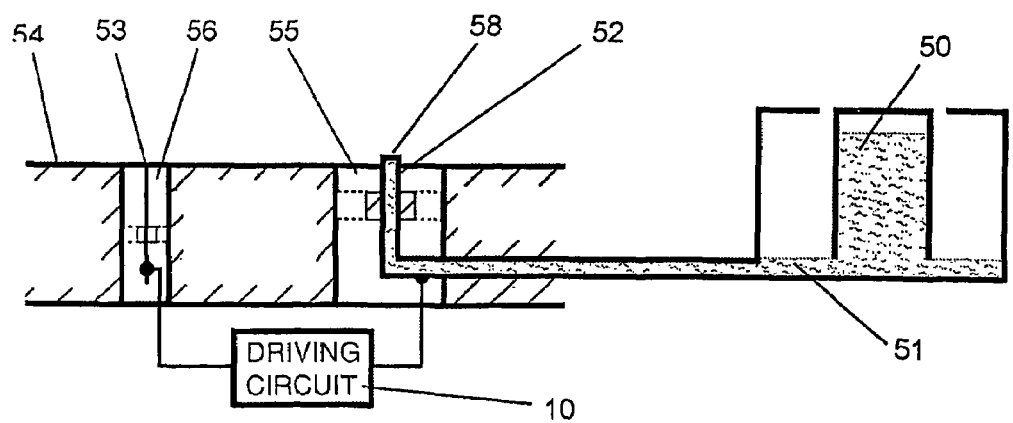

This embodiment is particularly useful for delivering a specific quantity of liquid. For example, where an exact dose of aroma or chemical or chemical mixture is required, this method provides a more simple alternative to the pump 31 shown in FIG. 3.

The outlet surface 64 of this example is curved with a convex profile. The spray electrode 62 and discharge electrode 63 lie in hemispherical recesses 65 and 66 respectively, and both electrodes are shown flush with the outlet surface 64 in this example. However, as indicated in the previous figures, both electrodes 62 and 63 can lie proud of or withdrawn from the outlet surface 64 provided that there is sufficient charge retention to modify the local electric field and maintain a stable set-up as described with reference to FIG. 3.

The driving circuit 10, as described with reference to FIG. 2, is connected between the two electrodes 62 and 63.

Figure 7:
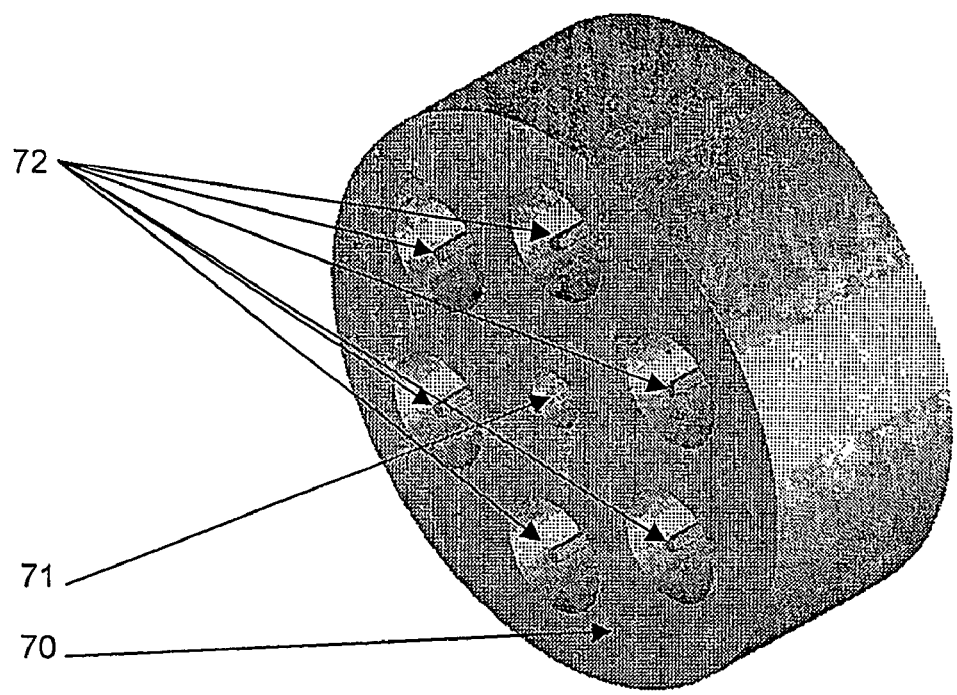

FIG. 7 shows an illustration of the outlet surface and electrodes of an alternative device embodying this invention. Here a plurality of spray electrodes 72 are spaced around a single discharging electrode 71. The outlet surface 70 shown here is flat but can take any desirable or aesthetic form provided it holds sufficient charge to distort the local electric field and maintain a stable set-up as described with reference to FIG. 3.

Electrical connections are made between a driving circuit as described with reference to FIG. 2 and the discharging electrode 71 and any of the spray electrodes 72 which is required to be active. The other spray electrodes 72 are electrically floating and left to find their own potential. In this manner, the invention provides a means of vaporising one or more of a variety of different liquids whose diffuse vapour products are to be mixed in the surrounding air. Such a device is ideal for creating aromatic blends in the vapour phase. Furthermore, the delivery rate to each spray electrode 72 can be controlled (by a microprocessor replacing the switch 21 in the driving circuits for example) so that the relative strengths of each aroma can be minutely adjusted until the desired effect is created. Such a device has useful application in the fragrance industry.

This arrangement can be reorientated to provide a linear array of spray electrodes, with each spray electrode having its own discharging electrode, which is sometimes preferable for reasons of controlling the potential difference between each electrode pair, or simply for aesthetic reasons.

Alternatively, several liquids may be mixed by providing a plurality of reservoirs, each reservoir being connected to a single conduit by a respective pump.

Figure 8:
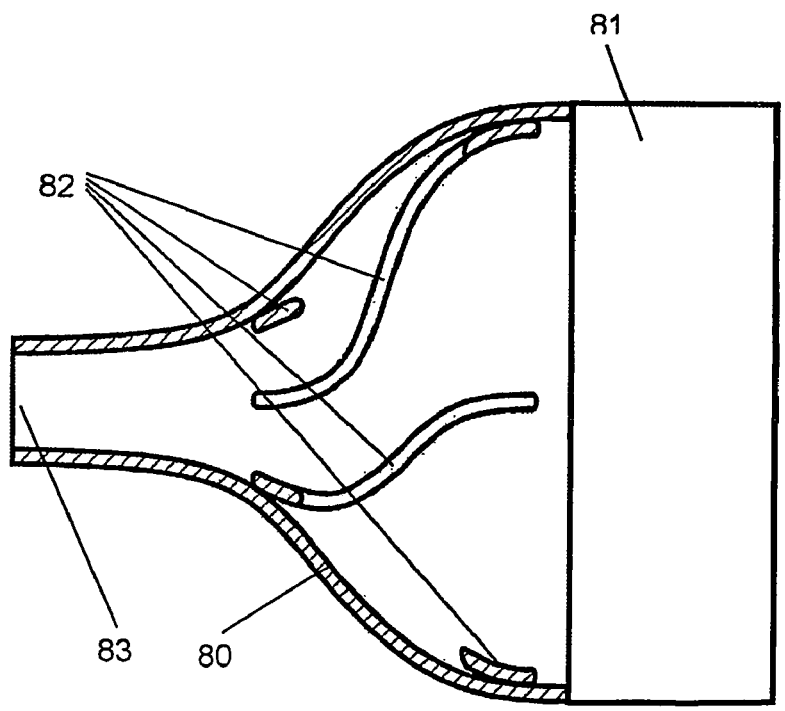

FIG. 8 shows a diagrammatic, cross-sectional view of a cap 80. This can be attached to the outlet surface of the multiple spray device illustrated in FIG. 7. This has a number of advantages. The first of these occurs if there is a possibility of damaging physical contact with the electrodes, where such a cap can prevent any undesirable interference. Furthermore, the cap 80 also provides a means of channelling the combined chemicals towards a particular space or place. This is useful, for example, for delivering aroma blends or other chemicals or chemical mixtures to a real or artificial nose, which can be placed near or over the outlet 83.

The cap 80 also provides an optional means, by way of the vortex fins 82 located on the inside of the cap 80, to stir up the various chemicals being emitted by the device. Where, for example, a blend of aromas is being created in the vapour phase, these fins ensure the product at the outlet 83 is better mixed.

The cap 80 can also be fixed to a single spray device such as described with reference to FIG. 1, where the electrodes need to be protected or the chemical output channelled towards a particular space or place, such as for remote odorising or fumigation of a room, for mechanical or human analysis of the dispersion, or for personal or individual inhalation of the product.

The dielectric material used to make the spray surface is selected such that charge leaks at a slow rate so that any charge deposited by way of ions or charged particles does not all migrate or leak away immediately. This ensures that the dielectric recesses retain a slight charge of the same polarity as the electrodes they house. This significantly alters the local electric field shape and ensures that further deposition is discouraged, most significantly without the need for extra electrodes such as described in WO00/64590.

A further advantage is that the device is polarity independent. In other words the spray electrode can be at any voltage (positive or negative) and the discharging electrode at any other voltage provided only that the potential difference is sufficient to create the spray in the first instance.

In experiments carried out on working prototypes we have found that the range of workable potential differences depends on the distance between the two electrodes, the depth to which they are recessed from the outlet surface and the size of the recesses themselves. Potential differences can range from 1-2 KV, up to 30 kV or more, and voltages can be both positive or negative in relative polarity.

The geometry of the spray surface is chosen such that the dielectric material of the outlet surface electrically shields one electrode from the other. This is important since it is desirable that charge is deposited on this spray surface to affect the local electric field. This means that where the recess is large, (i.e. the tip of the electrode has a large air gap between it and the outlet surface), the electrode should be well recessed, by 1 mm or more. But where the outlet surface is close to the electrode, the electrode can in fact be slightly proud of the housing.

Choice of materials is important but non-trivial since it depends on a variety of different factors. The intention is to allow charge to build up on the outlet surface of the device and in the electrode recesses, but not to reach levels that shield the electrodes themselves. Consequently, mid-range resistivity plastics or other dielectrics are most suitable.

It should also be noted that both the surface resistance and bulk resistivity are important. For instance, a plastic with very high bulk resistivity can be surface modified to have a low surface resistance, in which case the surface resistance will be the predominant path for charge leakage. Both paths (surface and bulk) must therefore be considered when selecting materials and designing the outlet surface.

A non-exhaustive list of materials which are suitable for this invention include acrylic, acrylonitrile butadiene styrene (ABS), ceramics and ceramic blends, glass/mineral/mica reinforced polyethylene terephthalate (PET), nylon (6, 11, 12 & 66), poly ether+styrene-butadiene blends, polyacetyl-polytetrafluoroethylene (PTFE) blends, polybutalene terephthalate (PBT) and glass/mineral/mica blends, polycarbonate and ABS blends, ABS and glass blends, polyetherimide, polyethylene, polyketone, polyphenylene sulfide and glass blends, polyphthalamide, polypropylene, polystyrene, polysulfone and glass blends, polyvinylidene fluoride (PVDF), styrene acrylonitrile, and blends thereof with each other or with glasses, organic molecules and minerals, for example, such as for changing the colour of the plastic.

These materials have surface resistances ranging from approximately $10^4$ to 14 $\Omega$, and bulk resistivities ranging from $10^5$ to $10^{15}$ $\Omega$m, and many can be used without any modification.

Where a material with very high bulk resistivity is selected its surface can be modified to reduce its resistance to make it more suitable for use. Alternatively, a more resistive material can be used in a thin layer to cover a conductive material. This has advantages where the liquid being sprayed is chemically corrosive, and a thin layer of PET is used as a protective layer over a more conductive plastic like nylon, for example.

Liquids that are suitable for this device can vary quite considerably in physical properties. Any liquid that forms a stable spray when emitted from a conductive electrode subjected to a strong electric field can be vaporized using this method. In the case of aromas, these oils can be mixed with a solvent like ethanol and are volatilised very well using this method. Other solvents include glycol ethers, propylene glycols, polyethylene glycols, 3-methoxy-3-methyl butanol, isododecane, diethylphthalate, isopropyl myristate and blends thereof.

It should also be noted that low volatility or non-volatile chemicals can be delivered in this manner by mixing with or suspending in a volatile solvent.

Embodiments can be designed to sit on surfaces, such as coffee tables; attached to walls, such as in a bathroom; suspended, such as in a wardrobe; or carried on the person. The same geometry can function in all these aspects making the design exceedingly flexible.

Such flexibility is facilitated partly due to the function of the dielectric material of the outlet surface, which helps to create an electrical pressure on the charged particles away from the outlet surface, whatever its orientation, and also due to the wide range of flow rates at which the liquid can be delivered to the spray electrode.

Our experiments have shown that the pressure head of liquid at the spray electrode can vary by around ±30 mm. Obviously, changes in the pressure head affect the rate at which the volatile liquid is delivered, so in many applications it is better to keep the pressure head as consistent as possible. However, as the device is electronically driven, it is possible to adjust the duty cycle to compensate for such changes.

The device itself can be miniaturised so that it can be easily carried on the person, and such that it can be used to discretely deliver whatever chemical or chemical combination is required.

Other applications and modifications thereof will be apparent to persons skilled in the art.

The invention claimed is:

1. An atomization device comprising: a) a conduit that contains, in use, liquid to be atomized; b) a spray electrode; and, c) a discharge electrode; each electrode being adjacent to a dielectric on or within the atomization device, wherein the electrodes are connected in an electrical circuit to enable a potential difference to be applied between the spray electrode and the discharge electrode to atomize the liquid and to generate charge carriers of a first polarity in the proximity of the spray electrode and ions of a second polarity in the proximity of the discharge electrode, and wherein some of the first polarity charge carriers deposit on the dielectric adjacent to the spray electrode and some of the second polarity ions deposit on the dielectric adjacent to the discharge electrode so that the atomized liquid is repelled from the dielectric adjacent to the spray electrode and electrically discharged by second polarity ions that are repelled by the dielectric adjacent to the discharge electrode.

2. An atomization device according to claim 1, wherein the atomization device further comprises a housing made of dielectric material defining respective recesses in which the electrodes are mounted.

3. An atomization device according to claim 2, wherein the tips of the spray and discharge electrodes are substantially flush with the top of the recesses.

4. An atomization device according to claim 1, wherein the conduit is the spray electrode.

5. An atomization device according to claim 1, wherein the conduit is made from conductive plastic.

6. An atomization device recording to claim 1, wherein the first polarity is positive and the second polarity is negative.

7. An atomization device according to claim 1, wherein the atomization device further comprises a reservoir connected to the conduit, the reservoir for containing the liquid to be atomized.

8. An atomization device according to claim 7, wherein the atomization device further comprises a pump for conveying the liquid to be atomized from the reservoir to the conduit.

9. An atomization device according to claim 7, wherein the conduit is a capillary so that the liquid to be atomized is conveyed from the reservoir to the conduit by capillary action.

10. An atomization device according to claim 7, wherein the reservoir is arranged relative to the conduit so that the liquid to be atomized is conveyed from the reservoir to the conduit under the influence of gravity.

11. An atomization device according to claim 1, wherein the atomization device comprises a plurality of reservoirs, each reservoir being connected to a respective pump that conveys liquid to be atomized from each reservoir to the conduit.

12. An atomization device according to claim 1, wherein the atomization device comprises a plurality of conduits and spray electrodes.

13. An atomization device according to claim 12, wherein the atomization device further comprises a plurality of reservoirs, each reservoir being connected to a corresponding conduit.

14. An atomization device according to claim 1, wherein the dielectric material has a surface resistance in the range of 10.sup.4.OMEGA. to 10.sup.14.OMEGA.

15. An atomization device according to claim 1, wherein the dielectric material is nylon 6, nylon 11, nylon 12, nylon 66 or a polyacetylpolytetrafluoroethylene blend.

16. An atomization device according to claim 1, wherein the dielectric material has been treated such that its surface resistance is in the range of 10.sup.4.OMEGA. to 10.sup.14.OMEGA.

17. An atomization device according to claim 1, wherein the atomization device further comprises a measuring system for measuring the flow rate of the liquid flowing through the conduit and a duty cycle modulator connected to the measuring system for controlling the flow rate by adjusting the duty cycle of the potential difference applied between the spray and discharge electrodes.

18. An atomization device according to claim 17, wherein the measuring system comprises a current monitor arranged to measure the current flowing to the spray electrode.

19. An atomization device, according to claim 1, wherein the atomization device further comprises a cap through which the atomized liquid is directed.

20. Use of an atomization device according to claim 19, and further wherein the atomization device comprises a plurality of reservoirs, each reservoir being connected to a respective pump that conveys liquid to be atomized from each reservoir to the conduit, to deliver a mixture of at least two atomized liquids.

21. Use of an atomization device according to claim 19 to direct the atomized liquid to a predefined region, for remote odorizing or fumigation of a room, for mechanical or human analysis or for personal or individual inhalation of the atomized liquid.

22. Use of an atomization device according to claim 1 to atomize an aromatic oil.

23. Use of an atomization device according to claim 1, to atomize an agricultural chemical.

24. Use of an atomization device according to claim 1, to atomize a pharmaceutical product.

25. Use of an atomization device according to claim 1, to atomize a pest control or pesticide chemical.

26. Use of an atomization device according to claim 1 to deliver the atomized liquid to a real or artificial nose.

27. Use of an atomization device according to claim 1 to vaporize a liquid by atomizing it.

28. The atomization device of claim 1 where the dielectric is shaped so that approximately all of the surface of the first electrode is hidden from all points on the surface of the second electrode.

29. The atomization device of claim 1 where the potential voltage between the electrodes is between approximately 1 kilo-volt to approximately 30 kilo-volts.

30. The atomization device of claim 1 where the potential voltage between the electrodes is greater than approximately 30 kilo-volts.

31. An atomization device comprising:

A dielectric with a surface;

a first and second electrode mounted in immediate proximity to said dielectric surface, where the first electrode is in close proximity to a conduit that, in operation, emanates atomized liquid droplets which are charged by the first electrode and the second electrode is a discharge electrode that emanates ions of opposite polarity to the charged droplets, where the first and second electrodes are operatively connected in an electric circuit that, when energized, produces an electric field between the first and second electrode and causes charge carriers to emanate from the first electrode to collect on the dielectric surface in an area adjacent to the first electrode, ions that emanate from the second electrode to collect on the dielectric surface adjacent to the second electrode and a plurality of charged droplets emanating from the conduit to be repelled from the dielectric surface adjacent to the first electrode.

32. The atomization device of claim 31 where the first electrode and the conduit are an integrated component.

33. The atomization device of claim 32 where the first electrode is attached to the dielectric surface within a first recess in said surface.

34. The atomization device of claim 33 where the second electrode is attached to the dielectric surface within a second recess in said surface.

35. The atomization device of claim 33 where the tip of the first electrode is approximately flush with the tangential plane of the dielectric surface immediately surrounding the first recess.

36. The atomization device of claim 35 where the tip of the second electrode is approximately flush with the tangential plane of the dielectric surface immediately surrounding the second recess.

37. The atomization device of claim 31 where the first and second electrode are attached to the dielectric surface within a corresponding first and second recess in the dielectric surface.

38. The atomization device of claim 37 where the tip of the first electrode and the tip of the second electrode are approximately flush with the tangential plane of the dielectric surface immediately surrounding their respective recesses.

39. The atomization device of claims 31, 32, 33, 35 or 37 where the electric circuit, when energized, further causes a plurality of charged droplets that are emitted from the conduit to be partially discharged by a plurality of ions emanating from the second electrode.

40. The atomization device of claim 39 where the dielectric surface has a surface resistance of approximately $10^4$ to approximately $10^{14}$ Ohms.

41. The atomization device of claim 40 where electric field comprises field lines that are induced by the voltage source and are primarily extended away from the dielectric.

42. The atomization device of claim 40 where electric field comprises field lines and where the dielectric is shaped so that substantially all of the field lines between the first electrode and the second electrode are not normal to the surface of either the first electrode or the second electrode.

43. The atomization device of claims 31, 32, 33, 34, 35, 36, 37, or 38 where the dielectric surface has a surface resistance in the range of approximately $10^4$ to approximately $10^{14}$ Ohms.

44. The atomization device of claim 43 where the field lines of the electric field induced by the voltage source are primarily extended away from the dielectric.

45. The atomization device of claim 43 where the dielectric is shaped so that substantially all of the field lines between the first electrode and the second electrode are not normal to the surface of either the first electrode or the second electrode.

46. A method of emitting atomized droplets comprising:
emanating a plurality of charge carriers of a first polarity from an electrode;
collecting a first portion of the plurality of charge carriers on the surface of a dielectric, the surface being adjacent to a conduit; and
electrostatically deflecting from the dielectric surface adjacent to the conduit a plurality of charged droplets emanating from the conduit.

47. The method of claim 46 where the first electrode and the conduit are an integrated component.

48. The method of claim 46 farther comprising:
emitting ions of a second polarity from a second electrode where the second polarity is opposite the first polarity; and
using the emitted ions to substantially discharge the deflected droplets.

49. The method of claim 48 where the first electrode and the conduit are an integrated component.

50. The method of claim 48 where the using step occurs in an electric field formed by applying a voltage between the first electrode and a second electrode that is in close proximity with the conduit.

51. An atomization device that when energized, performs the method of claims 46-50.

52. An atomization device comprising:
a conduit that emits charged droplets of a first polarity;
an electrode adjacent to the conduit that emanates charge carriers of the first polarity;
a first dielectric surface adjacent to the conduit and the electrode on which reside a plurality of the emanated charge carriers; and
an electric field produced by the plurality of the residing emanated charge carriers that repels from the first dielectric surface a plurality of the emitted charged droplets.

53. The atomization device of claim 52 where the first electrode and the conduit are an integrated component.

54. The atomization device of claim 52 further comprising:
a discharge electrode that emanates a plurality of charge carriers of a second polarity that is opposite to the first polarity;
a second dielectric surface adjacent to the discharge electrode on which reside a plurality of charge carriers that have emanated from the discharge electrode; and
an electric field produced by the plurality of emitted charge carriers that repels from the second dielectric surface at least one emanated charged carrier of the second polarity.

55. The atomization device of claim 54 where the first electrode and the conduit are an integrated component.

56. The atomization device of claims 52, 53, 54 or 55 where the dielectric surface has a surface resistance of approximately $10^4$ to approximately $10^{14}$ Ohms.

57. The atomization device of claim 56 where the conduit resides in a first recess formed in the dielectric.

58. The atomization device of claim 56 where the first electrode resides in a first recess in the dielectric surface and the second electrode resides in a second recess in the dielectric.

59. The atomization device of claim 58 where the tips of the first and second electrodes are approximately flush with the dielectric surface surrounding the first and second recesses, respectively.

60. The atomization device of claim 56 where the dielectric surface has a surface resistance of approximately $10^4$ to approximately $10^{14}$ Ohms.

61. The atomization device of claims 32, 33, 47, 53 or 55 where the charge carrier is a charged droplet.

62. The atomization device of claim 61 where the dielectric surface has a surface resistance of approximately $10^4$ to approximately $10^{14}$ Ohms.

* * * * *